(12) United States Patent
Dardick et al.

(10) Patent No.: US 9,944,940 B2
(45) Date of Patent: Apr. 17, 2018

(54) EFFECT OF PPEGID1C ON VEGETATIVE GROWTH OF FRUIT TREES

(71) Applicant: The United States of America, as Represented by the Secretary of Agriculture, Washington, DC (US)

(72) Inventors: Christopher D. Dardick, Shenandoah Junction, WV (US); Ralph Scorza, Shepherdstown, WV (US); Courtney A. Hollender, Brunswick, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 134 days.

(21) Appl. No.: 14/737,176

(22) Filed: Jun. 11, 2015

(65) Prior Publication Data
US 2016/0362701 A1    Dec. 15, 2016

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8218* (2013.01)

(58) Field of Classification Search
None
See application file for complete search history.

(56) References Cited

PUBLICATIONS

Emery et al (2003, Current Biology 13:1768-1774).*
Griffiths, Jayne et al., Genetic Characterization and Functional Analysis of the GID1 Gibberellin Receptors in Arabidopsis, The Plant Cell, (2006), 18:3399-3414
Hirano, Ko et al., GID1-mediated gibberellin signaling in plants, Trends in Plants Sciences, (2008), 13(4):192-199.
Li, Aixia et al., Molecular characterization of three Gibberellin-Insensitive DWARF1 homologous genes in hexaploid wheat, Journal of Plant Physiology, (2013), 170:432-443.
Scorza, Ralph et al., Molecular characterization of three Gibberellin-Insensitive DWARF1 homologous genes in hexaploid wheat, J. Amer. Soc. Hort. Sci., (2002), 127(2): 254-261.
Tworkoski, Thomas et al., Root and Shoot Characteristics of Peach Trees with Different Growth Habits, J. Amer. Soc. Hort. Sci., (2001), 126(6):785-790.
Hollender, Courtney A., et al., "A brachytic dwarfism trait (dw) in peach trees is caused by a nonsense mutation within the gibberellic acid receptor PpeGID1c", New Phytologist, (2015), pp. 1-13.

* cited by examiner

*Primary Examiner* — Russell Kallis
(74) *Attorney, Agent, or Firm* — John D. Fado; David L. Marks

(57) ABSTRACT

The genetic basis for a recessive dwarf trait (dw) in peach (*Prunus persica*) was determined. Using a sequencing-based bulk-segregant mapping strategy, dw was positioned on the distal end of peach chromosome 6. At the center of the mapped locus, a SNP leading to a premature stop codon was identified within the coding region of a homolog of the Giberellic Acid (GA) receptor GID1 (GA Insensitive Dwarf 1). Silencing of GID1c in the closely related species *Prunus domestica* (plum) led to dwarf phenotypes with shortened internodes similar to dw/dw peaches. The degree of GID1c silencing corresponded to the degree of dwarfing. Anatomical expression studies showed that GID1c was highly expressed in all actively growing peach tissues, but more predominant in apical meristems and roots. These data establish that GID1c serves a primary role in the rapid growth and elongation of peach vegetative tissues, thus providing new methods to control tree size without impacting flower or fruit development.

10 Claims, 7 Drawing Sheets
(5 of 7 Drawing Sheet(s) Filed in Color)

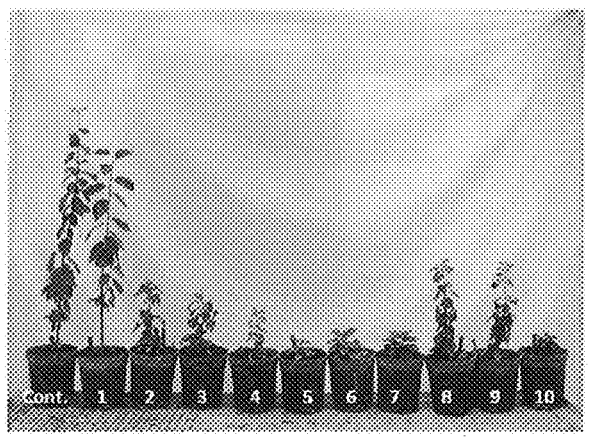
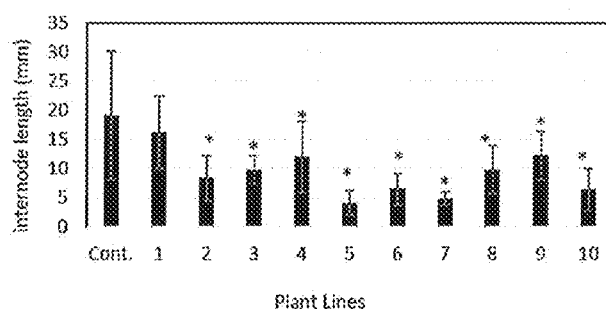
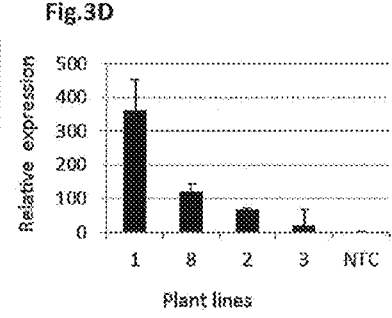
Fig. 3A-D

```
Score     Expect    Identities      Gaps          Strand  Frame
744 bits(824) 0.0()  797/1045(76%)  20/1045(1%)   Plus/Plus
Features:
Query   1    ATGGCTGGGACCAACGAAGTCAACGTTAATGAATCCAGGACGGTGGTTCCATTGAATACA   60
             |||||||| |  ||  |||| |||||| |||||||||||  || ||| |||||  ||||||
Sbjct   1    ATGGCTGGCAGTAATGAAGTCAACGTCAATGAATCCAAGAGGGTCGTTCCGCTTAATACA   60

Query   61   CGGTTCCATCTCCAATTTCAAGTTGTCTTACAATCTTCTTCGTCGACCTGATGGGACT   120
             |||||  |||||||||||||||||| ||||||||||||| || || || |||||||| |
Sbjct   61   CGGTACTCATCTCCAATTTCAAGCTAGCTTACAATCTCCTGCGCCGGGCTGATGGAACA   120

Query   121  TTTAACCGTCACTTGGCAGAATTCCTTGATCGGAAAGTGCCAGCCAATGCAAAACCCCCTT   180
             || ||||||  | |||||||| ||||||||  || ||||| |||||  ||||||| ||||||
Sbjct   121  TTCAACCGTGAGTTGGCAGAGTTTCTTGACCGCAAAGTCCCTGCCAATACAATTCCGCTT   180

Query   181  GATGCGGTGTCTCATTTGATGTCATCATTGACCGTGAAACTGGCCTGCTTACTCGAATC   240
             ||||||||| ||||||||||   ||  ||||| || || || || ||| |||| ||  |
Sbjct   181  GATGCGGTTTCTCATTTGAT--CA-CGTTCATAGAGGTACCGGACTCCTTAACCGCGTT   237

Query   241  TATCAACCAGCCAATGCTGAAGAATCTGTGCTGAAT-----ATTCTTAATCTTGACAAAC   295
             || |  ||  |||    ||||| ||| | ||| |||       ||| | |||||||| |||
Sbjct   238  TACCTACAGGCCC----CTGAA-AATGAG-GCTCAATGGGGATTGTGGATCTTGAGAAAC   292

Query   296  CTGTGAGCAATG---AGGTGGTGCCTGTCATAACTTTCTTCCATGGTGGAAGCTTTGCAC   352
             |  ||||||       || || ||||||||||||||||||||||||||| ||||| || |
Sbjct   293  CCTTGAGCACCACCAAGATTGTCCCAGTCATAACTTTCTTCCATGGTGGTAGCTTCACTC   352

Query   353  ACTCCTCTGCTAACAGTGGCATATATGAT---ATTCTGTGCCGCCGACTAGTTGGTATTTG   410
             | |||| ||  |||||||  || ||||||   |||||| ||  |||| || || ||  ||
Sbjct   353  ATTCCTCAGCCAACAGTGCCATCTATGATACATTCTGT---CGCCGTCTTGTTAATACATG   410

Query   411  CAAGGCTGTAGTGGTCTCTGTAAATTACCGCCGGGCACCTGAAAATCGATTCCTTGTGG   470
             ||||||||| || || || |||||||| | || || || |  ||||| |||||| ||||||
Sbjct   411  CAAGGCTGTTGTAGTGTCAGTAAATTATCGTCGATCGCCTGAACATCGATATCCTTGTGG   470

Query   471  CTATGATGATGGATGGACAGCCCTGCAGTGGGTCAACTCTAGATCGTGGCTAAAAGTAC   530
             ||||||||||||   || | | || ||||||||||  |||  ||  |  |||||   |||
Sbjct   471  ATATGATGATGGCTGGGCAACTCTCAAGTGGGTTAAATCAAGAACATGGCTTCGGAGTGG   530

Query   531  AAAGGACTCAAAAGTTCATATATATCCTGCTGGTGATAGCCCTGGTGGCAACATTGTACA   590
             ||||||||||||| ||||| | || || |||||||| | ||| || ||||||||| |  |
Sbjct   531  GAAGGACTCAAAGGTTCATGTTTACCTGGCTGGAGACAGTTCAGGTGGCAACATTGCTCA   590

Query   591  CAATGTTGCTTAAGAGCACTAGAACCTGAATTGATCTATGGAAATATACTGCTCAA   650
             | ||||| ||   |||  ||  ||| | || ||  ||| |||||||| || ||  |
Sbjct   591  CCATGTTGCAGTAAAAGCAGCTGAAGCAGAAGTTGAGGTATTGGGAAACATCCTTCTTCA   650

Query   651  CCCAATGTTTGGGGGCAGCAGAGAAGTAATCCAGAAGCGATTGGACGGAAATACTT   710
             ||| ||||||||| ||||||  | | ||  ||||||||  ||||||||||  ||||  |
Sbjct   651  CCCCATGTTTGGTGGCAAAACAGAACAGAATCAGAAAAGACATTGGATGGGAACTATTT   710

Query   711  TTGACATCAAGACCCGGGACTGGTATTGCAGACCTTTCCTGAAGCCAGACAG   770
             ||  || || ||||| ||  || || |||  |||||||| ||||||||  |||  |||
Sbjct   711  CGTTACAATTCAAGACCGCGATTCGTACTGGCAACCTTTCCTTCTGAAGCAGAGCAG   770

Query   771  GGACCACCCGGCATGTAACCCATTTGGTCCAAGGGGTAATAACCTTGAAGCTATCAAGTT   830
             | ||||||| ||||||||  ||||||||||| ||||| || |||  ||||| ||||| |||
Sbjct   771  AGACCACCCAGCATGTAATATATTTGGCCCCAGAGATAAAAGCCTTGAAGGGCTCAAATT   830

Query   831  CCCAAAGAGTCTTGTCGTGGTGGCTGGTTCGGATCTTGTTCAGGACTGGCAATTGGCTTA   890
             ||| || |||||||| |||||||||||||  |||||||||||||||||| || |||||| ||
```

Fig. 6

```
Sbjct  831   CCCCAAAAGTCTTGTTGTTGTGGCTGGTTTTGATCTTGTCCAAGATTGGCAATTGGCGTA  890

Query  891   TGCTAAAGGGCTTGAGAAGGCTGGCAAAAACATCAAACTTATGTATCTTGAGCAGCCCAC  950
             ||  |||||||  ||||  |  ||  |  |  || ||  ||||| ||||||||||
Sbjct  891   TGTGGAAGGGCTGAAGAATTCAGGTCAGGATGTGAAGCTCCTTTATCTAAAGCAGCCCAC  950

Query  951   AATTGGTTTCTACTTGCTGCCAAATAATGACCATTTCTACACCGTGATGGATGAGATAAG  1010
             ||| ||||||||||||  |||||||  |||| ||||||||    | ||||| ||||||||
Sbjct  951   AATCGGTTTCTACTTCCTGCCAAACAATGAGCATTTCTATTGTCTCATGGAGGAGATAAG  1010

Query  1011  TAAATTTGTGTGTTCCAACTGTTAA  1035
             || || ||   | |  |||||||||
Sbjct  1011  CAACTTCGTCAATCCTGACTGTTAA  1035
```

Fig. 6 (cont.)

SEQUENCE LISTING

```
<160> NUMBER OF SEQ ID NOS: 25

<210> SEQ ID NO 1
<211> LENGTH: 1035
<212> TYPE: DNA
<213> ORGANISM: Prunus persica

<400> SEQUENCE: 1
atggctggga ccaacgaagt caacgttaat gaatccagga cggtggttcc attgaataca      60
tgggtcctca tctccaattt caagttgtct tacaatcttc ttcgtcgacc tgatgggact     120
tttaaccgtc acttggcaga attccttgat cggaaagtgc cagccaatgc aaaaccagtt     180
gatggggttg tctcatttga tgtcatcatt gaccgtgaaa ctggcctgct tactcgaatc     240
tatcaaccag ccaatgctga agaatctgtg ctgaatattc ttaatcttga caaacctgtg     300
agcaatgagg tggtgcctgt cataattttc ttccatggtg gaagctttgc acactcctct     360
gctaacagtg gcatatatga tattctgtgc cgccgactag ttggtatttg caaggctgta     420
gtggtctctg taaattaccg ccgggcacct gaaaatcgat ttccttgtgc ctatgatgat     480
ggatggacag ccctgcagtg ggtcaactct agatcgtggc ttaaaagtac aaaggactca     540
aaagttcata tatatcttgc tggtgatagc tctggtggga acattgtaca caatgttgct     600
ttaagagcag tagaatctgg aattgatgta ttgggaaata tactgctcaa cccaatgttt     660 gggggggcagg agagaactga atctgagaag cgattggacg ggaaatactt tgtcaccatc     720
caagaccggg actggtattg gagagctttt ctccctgaag gggaagacag ggaccacccg     780
gcatgtaacc catttggtcc aaggggtaat aaccttgaag ctatcaagtt cccaaagagt     840
cttgtcgtgg tggctggttt ggatcttgtt caggactggc aattggctta tgctaaaggg     900
cttgagaagg ctggcaaaaa catcaaactt atgtatcttg agcaggccac aattggtttc     960
tacttgctgc caaataatga ccatttctac accgtgatgg atgagataag taaatttgtg    1020
```

```
tgttccaact gttaa                                                      1035
```

<210> SEQ ID NO 2
<211> LENGTH: 344
<212> TYPE: PRT
<213> ORGANISM: Prunus persica

<400> SEQUENCE: 2

```
Met Ala Gly Thr Asn Glu Val Asn Val Asn Glu Ser Arg Thr Val Val
1               5                   10                  15

Pro Leu Asn Thr Trp Val Leu Ile Ser Asn Phe Lys Leu Ser Tyr Asn
            20                  25                  30

Leu Leu Arg Arg Pro Asp Gly Thr Phe Asn Arg His Leu Ala Glu Phe
        35                  40                  45

Leu Asp Arg Lys Val Pro Ala Asn Ala Lys Pro Val Asp Gly Val Val
    50                  55                  60

Ser Phe Asp Val Ile Ile Asp Arg Glu Thr Gly Leu Leu Thr Arg Ile
65                  70                  75                  80

Tyr Gln Pro Ala Asn Ala Glu Glu Ser Val Leu Asn Ile Leu Asn Leu
                85                  90                  95

Asp Lys Pro Val Ser Asn Glu Val Val Pro Val Ile Ile Phe Phe His
            100                 105                 110

Gly Gly Ser Phe Ala His Ser Ser Ala Asn Ser Gly Ile Tyr Asp Ile
        115                 120                 125

Leu Cys Arg Arg Leu Val Gly Ile Cys Lys Ala Val Val Val Ser Val
    130                 135                 140

Asn Tyr Arg Arg Ala Pro Glu Asn Arg Phe Pro Cys Ala Tyr Asp Asp
145                 150                 155                 160

Gly Trp Thr Ala Leu Gln Trp Val Asn Ser Arg Ser Trp Leu Lys Ser
                165                 170                 175

Thr Lys Asp Ser Lys Val His Ile Tyr Leu Ala Gly Asp Ser Ser Gly
            180                 185                 190

Gly Asn Ile Val His Asn Val Ala Leu Arg Ala Val Glu Ser Gly Ile
        195                 200                 205

Asp Val Leu Gly Asn Ile Leu Leu Asn Pro Met Phe Gly Gly Gln Glu
    210                 215                 220

Arg Thr Glu Ser Glu Lys Arg Leu Asp Gly Lys Tyr Phe Val Thr Ile
225                 230                 235                 240

Gln Asp Arg Asp Trp Tyr Trp Arg Ala Phe Leu Pro Glu Gly Glu Asp
                245                 250                 255

Arg Asp His Pro Ala Cys Asn Pro Phe Gly Pro Arg Gly Asn Asn Leu
            260                 265                 270

Glu Ala Ile Lys Phe Pro Lys Ser Leu Val Val Val Ala Gly Leu Asp
        275                 280                 285

Leu Val Gln Asp Trp Gln Leu Ala Tyr Ala Lys Gly Leu Glu Lys Ala
    290                 295                 300

Gly Lys Asn Ile Lys Leu Met Tyr Leu Glu Gln Ala Thr Ile Gly Phe
305                 310                 315                 320

Tyr Leu Leu Pro Asn Asn Asp His Phe Tyr Thr Val Met Asp Glu Ile
                325                 330                 335

Ser Lys Phe Val Cys Ser Asn Cys
            340
```

<210> SEQ ID NO 3

-continued

```
<211> LENGTH: 1035
<212> TYPE: DNA
<213> ORGANISM: Prunus persica

<400> SEQUENCE: 3
atggctggca gtaatgaagt caacgtcaat gaatccaaga gggtcgttcc gcttaataca      60
tgggtactca tctccaattt caagctagct tacaatctcc tgcgccgggc tgatggaaca     120
ttcaaccgtg agttggcaga gtttcttgac cgcaaagtcc ctgccaatac aattccagtt     180
gatggggttt tctcatttga tcacgttgat agaggtaccg gactccttaa ccgggtttac     240
ctacaggccc ctgaaaatga ggctcaatgg ggattgtgg atcttgagaa acccttgagc      300
accaccaaga ttgtcccagt cataattttc ttccatggtg gtagcttcac tcattcctca     360
gccaacagtg ccatctatga tacattctgt cgccgtcttg ttaatacatg caaggctgtt     420
gtagtgtcag taaattatcg tcgatcgcct gaacatcgat atccttgtgc atatgatgat     480
ggctgggcaa ctctcaagtg ggttaaatca agaacatggc ttcggagtgg aaggactca     540 aaggttcatg tttacctggc tggagacagt tcaggtggca cattgctca ccatgttgca      600 gtaaaagcag ctgaagcaga agttgaggta ttgggaaaca tccttcttca ccccatgttt     660
ggtgggcaaa agagaacaga atcagaaaag agattggatg ggaagtattt cgttacaatt     720
caagaccgcg attggtactg gcgagctttt cttcctgaag gagaagacag agaccaccca     780
gcatgtaata tatttggccc cagagataaa gccttgaag gctcaaatt ccccaaaagt       840 cttgttgttg tggctggttt tgatcttgtc caagattggc aattggcgta tgtggaaggg     900
ctgaagaatt caggtcagga tgtgaagctc ctttatctaa agcaggccac aatcggtttc     960
tacttcctgc aaacaatga gcatttctat tgtctcatgg aggagataag caacttcgtc    1020
aatcctgact gttaa                                                    1035

<210> SEQ ID NO 4
<211> LENGTH: 249
<212> TYPE: DNA
<213> ORGANISM: Prunus persica

<400> SEQUENCE: 4
atggatggac agccctgcag tgggtcaact ctagatcgtg gcttaaaagt acaaaggact      60
caaaagttca tatatatctt gctggtgata gctctggtgg gaacattgta cacaatgttg     120
ctttaagagc agtagaatct ggaattgatg tattgggaaa tatactgctc aacccaatgt     180 ttgggggca ggagagaact gaatctgaga agcgattgga cgggaaatac tttgtcacca      240
tccaagacc                                                            249

<210> SEQ ID NO 5
<211> LENGTH: 2698
<212> TYPE: DNA
<213> ORGANISM: Prunus persica

<400> SEQUENCE: 5
cttgtatgct aaaatacgcc agccctctta tcctgcaccc gccccacaca agcacactct      60
ctattgctct gttttattgt agtgagattt gtcatttcat cacatgaatg cagagagagg     120
tttcccctag agattagggg cttgttttgt ctgggaccaa tgggttaacg aagtacgatc     180
taaaagttgg agagattcaa aggttaggtg cagcctggct ggctttgctt cttatttgag     240
tgtgaatacg tgaggctttg ttttctgaa gtgggtttgc tctcagagga tctgtgttgg      300
gttttctact agctaagctt tggtgtgga atttcttcag accggtttcc atggctggga     360
```

```
ccaacgaagt caacgttaat gaatccaggg taaccacttt ttctttgatc ttttgtttaa    420
ttcgaagttt ggttttggct cagcttctct gggttttggt ttagggtgat ggtttgctta    480
tcttaatggg ttctctgtgt tatggggttt ggtttgtggt tttgttataa aaagccagaa    540
tttgttcttg tttctttggt tggtctgaag actttgttct tgttttagtt gaggtttgta    600 ccagttttc tttaggattt gaacagatat ggtattgggt ttgttatact tgttcgagtt    660
catcaggttt ttgaatctct tcttgtttgg agatgtgact gggatttagt gttgcggttt    720
tagcattggg atgggaggct gagtatctgc tgaacttcag cttcagcttc aagaaatttg    780
attagatgaa catgattgta tttgaagact ggtaatagat tttaggcttg tatggccaaa    840
tccactgctt tatgggaatg ctttagttga tttttgttttt tgtgctttct tgtcaaagtg    900
ttcatgtcct tcatttgtgg tggttccatg gtgtctctgt taccttgaaa gttgaaacaa    960
tagcaaaaag ctttgtttat agatgcaatt actctggtgt tggttggagt tcttgattct   1020
tagtcatgtt tatcttgtta tgttggaata tgaatttaac ataccttaatt ttgttttggg   1080 atcttgtgct ctatacagac ggtggttcca ttgaatacat gggtcctcat ctccaatttc   1140
aagttgtctt acaatcttct tcgtcgacct gatgggactt taaccgtca cttggcagaa   1200 ttccttgatc ggaaagtgcc agccaatgca aaaccagttg atggggttgt ctcatttgat   1260
gtcatcattg accgtgaaac tggcctgctt actcgaatct atcaaccagc caatgctgaa   1320
gaatctgtgc tgaatattct taatcttgac aaacctgtga gcaatgaggt ggtgcctgtc   1380
ataattttct tccatggtgg aagctttgca cactcctctg ctaacagtgg catatatgat   1440
attctgtgcc gccgactagt tggtatttgc aaggctgtag tggtctctgt aaattaccgc   1500
cgggcacctg aaaatcgatt tccttgtgcc tatgatgatg gatggacagc cctgcagtgg   1560
gtcaactcta gatcgtggct taaaagtaca aaggactcaa aagttcatat atatcttgct   1620
ggtgatagct ctggtgggaa cattgtacac aatgttgctt taagagcagt agaatctgga   1680
attgatgtat tgggaaatat actgctcaac ccaatgtttg gggggcagga gagaactgaa   1740
tctgagaagc gattggacgg gaaatacttt gtcaccatcc aagaccggga ctggtattgg   1800
agagcttttc tccctgaagg ggaagacagg gaccacccgg catgtaaccc atttggtcca   1860 agggggtaata accttgaagc tatcaagttc ccaaagagtc ttgtcgtggt ggctggtttg   1920
gatcttgttc aggactggca attggcttat gctaaagggc ttgagaaggc tggcaaaaac   1980
atcaaactta tgtatcttga gcaggccaca attggtttct acttgctgcc aaataatgac   2040
catttctaca ccgtgatgga tgagataagt aaatttgtgt gttccaactg ttaatagaat   2100
tgactttcat cgcgtgcggt gatatataac ctaagcttga catttcaccc ggaataatga   2160
agggtttgtt tgcagtacgt aagattgtgt agctatagtg attattacta ttgtattgat   2220
aattgtggta ctaaaagatc ctgctggggt ctggttcttg tctgaggagg actaggcttg   2280
gttgttggat gcaaaggtat atgtggatct gcatatagct ggatcagcat gttttgttct   2340
ggtgcaaatc ggagcttccg aaaatttggt attttggttc gataaagctt tgcagacagc   2400
aggatcgatt aactaaggtt agcagtccca cgacacttcc agatttgagg attccgacta   2460
ccggccacaa tgaagaggaa gacactcagg attgttggtg tgacacccac atccagtgac   2520
ttgctaatgt tatattatat atagctaatt cggaacatgg atggaaaatc atcctccatg   2580
gtattgttgt catgtattat tgtgtatact tttgtgctag attatataaa atggttgtgt   2640
attggctgtt gcctttgttg tttaagcttt ccagttactt ggtatgccaa tatttgat    2698
```

```
<210> SEQ ID NO 6
<211> LENGTH: 19
<212> TYPE: DNA
<213> ORGANISM: Prunus persica

<400> SEQUENCE: 6
ccgtttgcat agatccgtt                                                      19

<210> SEQ ID NO 7
<211> LENGTH: 17
<212> TYPE: DNA
<213> ORGANISM: Prunus persica

<400> SEQUENCE: 7
tggggattcg agatccc                                                        17

<210> SEQ ID NO 8
<211> LENGTH: 22
<212> TYPE: DNA
<213> ORGANISM: Prunus persica

<400> SEQUENCE: 8
tcaagtattg gaagcagttg tt                                                  22

<210> SEQ ID NO 9
<211> LENGTH: 21
<212> TYPE: DNA
<213> ORGANISM: Prunus persica

<400> SEQUENCE: 9
ttgcaaccat aggttgggac t                                                   21

<210> SEQ ID NO 10
<211> LENGTH: 19
<212> TYPE: DNA
<213> ORGANISM: Prunus persica

<400> SEQUENCE: 10
cagaatgaga aggcaaggc                                                      19

<210> SEQ ID NO 11
<211> LENGTH: 19
<212> TYPE: DNA
<213> ORGANISM: Prunus persica

<400> SEQUENCE: 11
atctccaatg caattcgcc                                                      19

<210> SEQ ID NO 12
<211> LENGTH: 23
<212> TYPE: DNA
<213> ORGANISM: Prunus persica

<400> SEQUENCE: 12
taagccacga tctagagttg acc                                                 23

<210> SEQ ID NO 13
<211> LENGTH: 18
<212> TYPE: DNA
<213> ORGANISM: Prunus persica

<400> SEQUENCE: 13
gtaaattacc gccgggca                                                       18
```

```
<210> SEQ ID NO 14
<211> LENGTH: 18
<212> TYPE: DNA
<213> ORGANISM: Prunus persica

<400> SEQUENCE: 14
gcccgaggca gagttatt                                                 18

<210> SEQ ID NO 15
<211> LENGTH: 17
<212> TYPE: DNA
<213> ORGANISM: Prunus persica

<400> SEQUENCE: 15
ggtccgtttc ctatgcg                                                  17

<210> SEQ ID NO 16
<211> LENGTH: 17
<212> TYPE: DNA
<213> ORGANISM: Prunus persica

<400> SEQUENCE: 16
cgccatggtt ggttttg                                                  17

<210> SEQ ID NO 17
<211> LENGTH: 19
<212> TYPE: DNA
<213> ORGANISM: Prunus persica

<400> SEQUENCE: 17
ccctcacctt ctctgcctc                                                19

<210> SEQ ID NO 18
<211> LENGTH: 19
<212> TYPE: DNA
<213> ORGANISM: Prunus persica

<400> SEQUENCE: 18
gctgcttcaa ggccttcat                                                19

<210> SEQ ID NO 19
<211> LENGTH: 21
<212> TYPE: DNA
<213> ORGANISM: Prunus persica

<400> SEQUENCE: 19
ggaccccact tgaatgaaat t                                             21

<210> SEQ ID NO 20
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 20
atggatggac agccctgc                                                 18

<210> SEQ ID NO 21
<211> LENGTH: 25
<212> TYPE: DNA
<213> ORGANISM: Artificial Sequence
<220> FEATURE:
```

```
<223> OTHER INFORMATION: Chemically Synthesized

<400> SEQUENCE: 21
ggtcttggat ggtgacaaag tattt                                        25

<210> SEQ ID NO 22
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 22
gctctataca gacggtggtt ccat                                         24

<210> SEQ ID NO 23
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 23
cccatcaact ggttttgcat tggc                                         24

<210> SEQ ID NO 24
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 24
gctggcagta atgaagtcaa cgtc                                         24

<210> SEQ ID NO 25
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 25
ctctgccaac tcacggttga atgt                                         24
```

EFFECT OF PPEGID1C ON VEGETATIVE GROWTH OF FRUIT TREES

BACKGROUND OF THE INVENTION

Field of the Invention

This invention relates to a novel gene PpeGID1c and its role in controlling growth and elongation of peach vegetative tissues and to new methods of manipulating tree size by silencing PpeGID1c.

Description of the Relevant Art

Trees in agricultural production systems require unique management and horticultural practices. These include grafting, pruning, training, harvesting, and spraying strategies specifically designed to manage and/or accommodate tree size and structure. Such practices are both costly and labor intensive. For example, many fruit and nut trees utilize dwarfing rootstocks to control tree size. This requires additional material and labor costs. Genetic manipulation of tree size either through breeding or biotechnology offers a promising approach to minimize the efforts needed to optimize tree growth (Webster, T. 2002. *Dwarfing Rootstocks: Past, Present and Future* 35:67-72). To date, only a few studies have investigated ways to genetically manipulate tree growth rates and overall height. These studies have involved the manipulation of genes involved with Gibberellic Acid (GA) hormone levels and/or response signaling pathways. GA is crucial for many aspects of plant development and growth. In plum and poplar, high levels or over-expression of GA2Oxidase (GA2Ox) genes, which code for enzymes that convert active forms of GA to an inactive form, resulted in reduced vigor, stature, and, in some cases, extreme dwarfism (Busov et al. 2003. *Plant Physiol.* 132:1283-1291; El-Sharkawy et al. 2012. *J. Exp. Bot.* 63:1225-1239; Zawaski et al. 2011. *Planta* 234:1285-1298). The same phenomenon has been observed in many herbaceous species when GA2Ox genes are up-regulated (Appleford et al. 2007. *J. Exp. Bot.* 58:3213-3226; Dijkstra et al. 2008. *Plant Cell Rep.* 27:463-470; Sakamoto et al. 2001. *Plant Physiol.* 125:1508-1516; Sakamoto et al. 2004. *Plant Physiol.* 134: 1642-1653; Wuddineh et al. 2015. *Plant Biotechnol. J.* 13:636-647; Otani et al. 2013. *J. Plant Physiol.* 170:1416-1423; Lee and Zeevaart. 2005. *Plant Physiol.* 138:243-254). Complementing these studies, high levels of GA2Oox, an enzyme for the biosynthesis of active GAs, are associated with increased height and branch diameter in pine trees (Park et al. 2014. *Tree Physiol.* 35:86-94). Additionally, overexpression of dominant negative mutant versions of a GA response repressor called DELLA such as repressor of ga1-like (rgl) and ga insensitve (gai), led to dwarfism in both trees and herbaceous species (Zawaski et al., supra). A significant limitation of these methods for use in dwarfing fruit trees is that the GA hormone is required for proper flower and fruit development (Bulley et al. 2005. *Plant Biotech. J.* 3:215-223).

Breeding efforts using naturally occurring germplasm to reduce tree size and optimize shape have been carried out in a number of tree crops, particularly those for fruits and nuts. In peach, a handful of these traits have been genetically characterized including several dwarf traits, called dw, which have been used to breed new varieties with the potential to increase productivity and reduce labor costs. At least three dw loci, called dw, dw2, and dw3, have been reported as single recessive genes (Scorza et al. 2002. *J. Am. Soc. Hortic. Sci.* 127:254-261; Chaparro et al. 1994. *Theor. Appl. Genet.* 87:805-815; Shimada et al. 2000. *J. Japanese Soc. Hortic. Sci.* 69:536-542; Monet et al. 1988. *Agronomie* 5:727-731; Hansche, P. E. 1988. *Hortscience* 23:604-606).

Peach trees homozygous for dw or dw2 display brachytic dwarfism (FIG. 1). They have extremely short internodes, thickened stems, reduced higher order branching, and elongated leaves. dw3 peach trees display a distinct dwarf phenotype marked by narrow branches and willowy leaves (Chaparro et al., supra). Several different sources of dw have been described (including ornamental types from Japan and China); however, no tests for allelism have been reported. One of the dw loci was genetically mapped by Shimada et al. (2000, supra) in a cross between the Japanese cultivars 'Akame' and the ornamental dwarf type 'Jusietou' and later positioned to the proximal end of linkage group 6 (Dirlewanger et al. 2004. *Proc. Natl. Acad. Sci. USA* 101:9891-9896). To date, the identity of all dw genes remains unknown.

The cultivation of tree species for agricultural production is expensive in large part because of manual architectural manipulations required to maximize productivity and harvesting efficiency. State-of-the-art pruning requires tremendous amounts of manual labor and costs. Harvesting fruit and nuts from large spreading trees often requires the use of ladders or elevated platforms. When using mechanized harvesting equipment such as shakers, substantial losses can be incurred from fruit bruising when dropped from high or dense canopies. Trees also require tremendous amounts of land space which leads to excessive use of fertilizers and pest control chemical inputs. As has been accomplished for cereals and other crops, genetic architectural improvements to enable high density production systems and mechanization stand to revolutionize the way in which fruits, nuts, and other tree-based crops are produced. Easier management will translate to immediate cost savings for growers and consumers. Developing crop trees with different degrees of dwarfing would lead to high density production, reduced manual labor costs, and reduced amounts of chemical (fertilizers and pest control) inputs needed and therefore a substantial cost savings and an environmental benefit. The ability to rationally manipulate tree size could also benefit the ornamental tree industry, enabling more aesthetically appealing landscape designs. To meet these challenges the development of improved varieties is vital.

SUMMARY OF THE INVENTION

We have identified GID1c (SEQ ID NO:1) as the causative gene for the brachytic dwarf phenotype in the peach and confirmed that silencing its expression results in *Prunus* trees having a dwarf appearance.

In accordance with this discovery, it is an object of the invention to provide a method to routinely control tree size in *Prunus* trees comprising silencing of the expression of the GID1c gene (SEQ ID NO:1) in *Prunus* trees or germplasm to obtain brachytic dwarfism in *Prunus* trees while still retaining normal flower and fruit development.

It is another object of the invention to provide an isolated or recombinant polynucleotide molecule comprising a 249 consecutive base pair fragment (SEQ ID NO:4) of the GID1c gene (SEQ ID NO:1).

It is an additional object of the invention to provide hairpin nucleic acid construct comprising a GID1c polynucleotide gene sequence comprising a 249 consecutive sense nucleotide fragment (SEQ ID NO:4) of the GID1c gene of *Prunus* and the antisense-complement thereof, such that first and the second polynucleotide sequences hybridize when transcribed into a ribonucleic acid to form the hairpin-like double stranded ribonucleotide molecule.

It is an object of the invention to provide transformed *Prunus* plant cells and *Prunus* plants having the characteristics of brachytic dwarfism of short internodes, thick woody stems, elongated leaves, dwarf root systems and slower growth.

It is a further object of the invention to control tree size in *Prunus* cultivars including *Prunus persica* (peach), *Prunus domestica* (plum), *Prunus avium* (cherry), *Prunus salicina* (Japanese plum) and *Prunus armeniaca* (apricot).

It is another object of the invention to provide a method of producing a *Prunus* plant having the characteristics of brachytic dwarfism comprising: constructing a recombinant vector comprising a construct comprising the 249 base pair consecutive nucleotide fragment (SEQ ID NO:4) of the GID1c gene of *Prunus*, transforming *Prunus* plant cells with the recombinant vector and expressing in the plant said construct encoding the GID1c gene sequence comprising a 249 bp consecutive sense nucleotide fragment of the GID1c gene of *Prunus* and the antisense-complement thereof, wherein the expressing induces RNA interference (RNAi) in the plant resulting in plants having the characteristics of brachytic dwarfism.

It is another object of the invention to provide a transgenic *Prunus* plant, produced by the methods of the invention, or the progeny thereof, comprising: the RNAi construct of the invention, said plants exhibiting changed plant architecture with short internodes compared to a wild-type non-transformed *Prunus* plant.

It is an additional object of the invention to provide a transgenic *Prunus* cell comprising the RNAi construct of the invention, wherein the transgenic plant regenerated from said cell exhibits suppression of the GID1c gene, said RNAi construct comprising the fragment of SEQ ID NO:4 resulting in a plant demonstrating changed plant architecture with short internodes, thick woody stems, elongated leaves, dwarf root systems and very slow growth, relative to the wild-type *Prunus* plant.

It is yet another object of the invention to provide plants, plant cells, and plant parts, and plant seeds which have been transformed by the GID1c RNAi construct of the invention.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1A shows a standard peach tree and FIG. 1B, a dwarf peach tree, from the mapping population at 4 years old. FIG. 1C shows a branch from a dormant 4 year old brachytic dwarf tree illustrating the phenotypic forked branching pattern and the short internodes between the white flower buds. FIG. 1D shows one year old peach trees from segregating populations: standard (left) and brachytic dwarf (right).

FIG. 2A shows the brachytic dwarf pnome map of variant frequency at each position on chromosome 6. The curve peak indicates a chromosome region that is highly linked to the dwarf phenotype. The large black diamond indicates the position of the nonsense mutation in Ppa018174. FIG. 2B is a diagram of chromosome 6 indicating the locations of the Ppa018174 gene, the brachytic dwarf mutation (gid1c) and HRM mapping markers (M1-6). The cM location of markers is based on recombination events between the locus and the marker in 109 trees from a segregating population.

FIGS. 3A-3C show that silencing of GID1c in plum results in decreased height and internode length. FIGS. 3C and 3D shows that GID1c expression analysis done by qPCR on several plant lines reveals that the degree of GID1c expression correlates with tree height. Controls in A and B are plums transformed with empty vectors. * indicates $p<0.05$

FIG. 6 shows the alignment of GID1c (top; SEQ ID NO:1) and GID1b (SEQ ID NO:3) cDNA sequences. The regions highlighted in gray denote regions of complementarity that fit the criteria for potential silencing (contiguous match >20 bp with <2 mismatches). The region we used for silencing is highlighted in yellow (SEQ ID NO:4). This region was chosen to avoid potential non-target silencing of GID1b since it lacks long contiguous matches.

DETAILED DESCRIPTION OF THE INVENTION

The rate and patterning of tree growth is critical for fruit and nut production, forestry plantations, and landscape architecture. To date, little is known about the genetic factors that contribute to variations in tree size and shape. Here we studied the genetic basis for a naturally occurring recessive dwarf trait (dw) in peach (*Prunus persica*). We had aimed to map and identify a dw allele originating from a California peach selection called 'Valley Red' (FIG. 1). The dw/dw trees have short internodes, thick woody stems, elongated leaves, dwarf root systems and very slow growth (only a few inches a year at most) but produce normal flowers and fruit. Here we describe the identification of peach dw as an allele of the Giberellic Acid (GA) receptor GID1c with a nonsense mutation. Mapping, functional confirmation and characterization of GID1c is further discussed as is the utility of manipulating GID1c expression for breeding trees with reduced statures. This dw trait was previously found to segregate as a single recessive gene (Scorza et al., supra) and treatment of dw/dw trees with GA did not stimulate growth, suggesting a possible alteration of GA perception and/or signaling (Scorza, unpublished).

Here we found that a nonsense mutation in an orthologue of the GA receptor GID1c is the causative agent for a brachytic dwarf phenotype in peach. Direct functional studies on GID1c function have been previously carried out in monocots such as rice, barley, and wheat as well as dicots including *Arabidopsis*, cotton, and aspen (Uguchi-Tanaka et al. 2005. *Nature* 437:693-698; Griffiths et al. 2006. *Plant Cell* 18:3399-3414; Nakajima et al. 2006. *Plant J.* 46:880-889; Chandler et al. 2008. *Mol. Plant* 1:285-294; Aleman et al. 2008. *Plant Mol. Biol.* 68:1-16; Moriat and Moritz. 2009. *Plant J.* 58:989-1003; Wu et al. 2011. *Plant Physiol.* 157: 2120-2130; Li et al. 2011. *Mol. Biol. Rep.* 38:191-197; Voegele et al. 2011. *J. Exp. Bot.* 62:5131-5147). This paper describes the first example of a naturally occurring tree trait linked to a GA response gene, as well as the first example of how silencing of GID1c could be used for reducing height in fruit trees without impacting flowering or fruiting.

Figure 4:
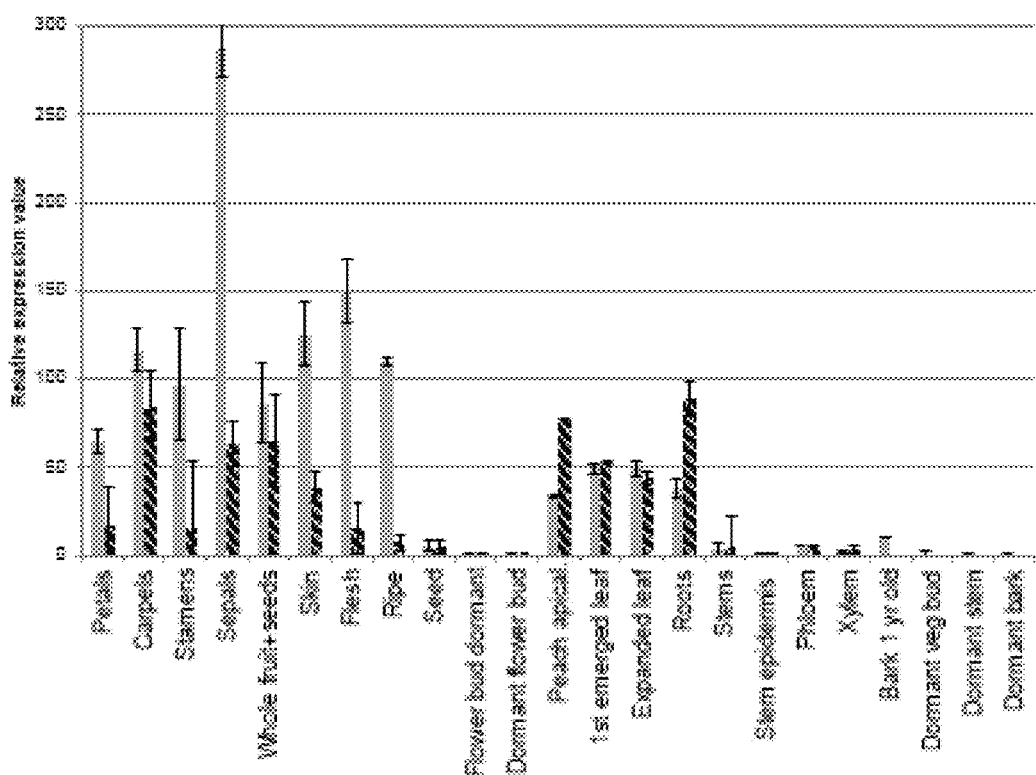
FIG. 4 shows the relative expression of native GID1b (solid bars) and native GID1c (hashed bars) as determined by qPCR in various peach tissues collected from standard trees. The data show expression of both family members which are likely to have overlapping functions but are predominantly expressed in different tissues.

GID1c was identified as the causative gene for the brachytic dwarf phenotype in peach by using a novel whole genome sequencing strategy, called pnome sequencing, that enables rapid simultaneous mapping and candidate gene identification. Using a sequencing-based bulk-segregant mapping strategy, dw was positioned on the distal end of peach chromosome 6. At the center of the mapped locus, a SNP leading to a premature stop codon was identified within the coding region of a homolog of the Giberellic Acid (GA) receptor GID1 (GA Insensitive Dwarf 1). These dwarf peach trees all contained a missense mutation that produced a stop codon early in the gene sequence, preventing the production of any viable GID1c protein. GID1 genes were previously shown to have diverged into two clades in dicots. The dw mutation was within a GID1 orthologue most similar to GID1c from *Arabidopsis thaliana*. *Arabidopsis* has three GID1 genes (a, b, c) where GID1a and GID1c were both previously shown to be associated with vegetative growth. The GID1 gene was first identified in dwarf rice plants (for which there is only a single GID1 gene), and further studied in *Arabidopsis* and wheat, as well as other crops. The peach genome contains two GID1 receptor genes, GID1b and GID1c while rice has only one GID1 gene. It appears that these two genes have different primary functions. The brachytic dwarf peach, although slow growing and small in stature, displays normal flower and fruit development. This finding is consistent with tissue-specific gene expression data that GID1c was significantly elevated in peach apical shoot tissues compared to GID1b, while GID1b expression was significantly greater in fruit and flower tissues (FIG. 4). The expression data presented here is consistent with data from Busov et al. (supra) who found that in poplar GID1c expression in the stem was greater (by two-fold or more) than GID1b. Combined, these data suggests that GID1c is the primary GA receptor in apical meristems and shoots, while GID1b is the primary receptor for flower and fruit development. However, since shoot growth still occurs in the PpeGID1c mutant and silenced *Prunus* trees it seems likely that PpeGID1b can partially compensate for the lack of PpeGID1c.

There are several distinct active forms of GA that feed into the GA response pathway, including $GA_1$, $GA_3$, and $GA_4$. The division of the roles of these the GID1b and GID1c receptors may be due to their specific affinities for the different forms of GA. We found that the dwarf peach trees were insensitive to $GA_3$, when applied in the form of Progib® (Valent BioSciences) to the apical meristems (data not shown) while peach shoots on standard trees elongated in response to $GA_3$. In peach, GID1c may be the only receptor that binds $GA_3$ in the shoot meristem. The limited internode elongation that occurs in the dwarf trees may come from the binding of GID1b to another form of active GA, possible $GA_4$. Nakajima et al. (supra) showed in vitro that within the pH range of 6.4-7.5 *Arabidopsis* GID1b has a ten-fold higher affinity for $GA_4$ compared to GID1a and GID1c. Additionally, AtGID1b associated with $GA_4$ more quickly than GID1a, which has overlapping functional roles as AtGID1c Nakajima et al. (supra). The pH in the shoot/stem/meristem may not be ideal for GID1b interaction and related responses, rendering GID1c the primary receptor. Alternatively, GID1b and GID1c could require the presence of differentially expressed regulatory DELLA proteins that may limit their roles in different tissues.

Figure 5:
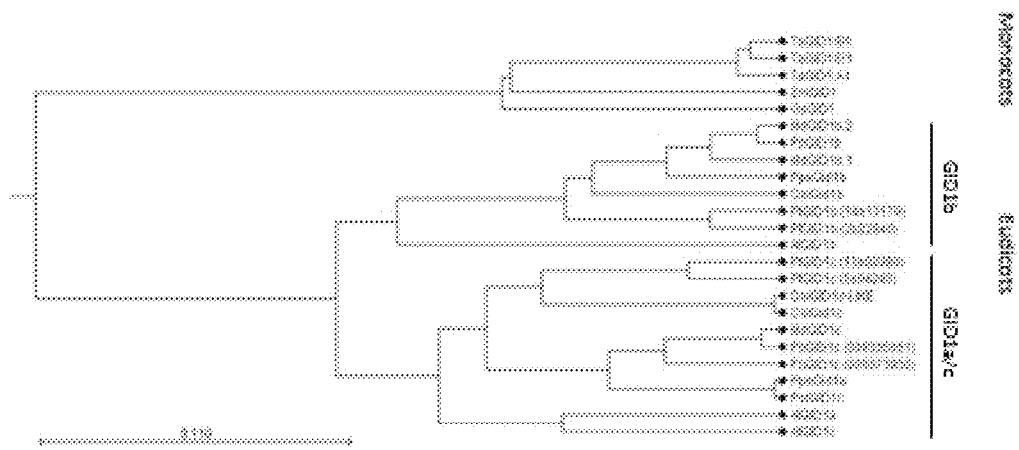
FIG. 5 shows a phylogenetic tree of GID1 proteins in monocots and dicots based on alignment of amino acid sequences. Gene numbers are in parentheses when more than one homolog was detected and is previously unannotated. The following species and protein sequences were used: Wheat: TAGID1 A1 (protein ID), TAGID1 B1, TAGID1 D1. Maize: ZmGID1. Rice: OsGID1. Apple: MdGID1b.1, MdGID1b.2, MdGID1c. Peach: PpeGID1 b, PpeGID1c. Orange: CsoGid1b, CsoGID1c-LIKE, Pear: PbGID1b, PbGID1b, PbGID1c, PbGID1c. Poplar: PtGID1b, PtGID1b, PtGID1c, PtGID1c, *Arabidopsis*: AtGID1a, AtGID1b, AtGID1c.

A second, and potentially applicable result of this study is that our GID1c RNAi knock-down plum lines showed varying degrees of dwarfing. Silencing of GID1c in the closely related species *Prunus domestica* (plum) led to dwarf phenotypes with shortened internodes similar to dw/dw peaches. The degree of GID1c silencing corresponded to the degree of dwarfing in transgenic plum trees. These data establish that GID1c serves a primary role in the rapid growth and elongation of peach vegetative tissues while GID1b likely functions to regulate GA perception in reproductive organ. The results establish that variations of GID1c expression could be used for breeding trees with desired heights. The utility of GID1c expression modulation could possibly extended beyond peach and plum trees as the genomes of other fruit crops such as apple and pear also show the presence of clear GID1c and GID1b homologues (FIG. 5).

To date there have been a few studies of molecular mechanisms of plant size in trees. Most have focused on the manipulation of GA signaling pathways downstream of GA perception. Some have produced gene candidates with the potential to reduce tree stature. For example, over expression of GA2Ox and non-functional DELLA genes produced dwarf trees (Busov et al., supra; El-Sharkawy et al., supra). However, pleiotropic affects caused by the transgenes or naturally occurring expression, including crucial flower and fruit development, accompanied their decreased heights, limiting their utility for fruit trees. Naturally dwarf *Prunus salicina* (El-Sharkawy et al., supra) trees found to have elevated GA2Ox levels displayed very small fruit unless the trees were sprayed with GA hormone, a step that would cause developmental problems in other parts of the plant as well as being expensive. GID1c may be a more ideal candidate gene for use in for tree height, because when absent, at least in peach, the trees are still able to develop normal fruit. By reducing GID1c expression in trees using biotechnology or selecting trees with naturally reduced expression, orchard management and maintenance costs could be reduced. Likewise, the need for dwarfing rootstocks and costly chemical and hormone sprays for size management could be eliminated.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature* (London) 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985.

A "construct" or "chimeric gene construct" refers to a nucleic acid sequence encoding a protein, here the GID1c protein, operably linked to a promoter and/or other regulatory sequences.

As used herein, the term "express" or "expression" is defined to mean transcription alone. The regulatory elements are operably linked to the coding sequence of the GID1c gene such that the regulatory element is capable of controlling expression of GID1c gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence (described above) which specifically induces gene expression in root tips. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

A "protein" or "polypeptide" is a chain of amino acids arranged in a specific order determined by the coding sequence in a polynucleotide encoding the polypeptide. Each protein or polypeptide has a unique function.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful transformation of *Prunus* with GID1c is a major step in manipulating tree shoot elongation and thus overall tree size in *Prunus*, thus ensuring the development of improved varieties of *Prunus*.

The creation of *Prunus* trees that are reduced in size with no effect on their fruit production enables high density production systems and reduced requirements for chemicals and labor costs resulting in easier management and cost savings.

EXAMPLES

Having now generally described this invention, the same will be better understood by reference to certain specific examples, which are included herein only to further illustrate the invention and are not intended to limit the scope of the invention as defined by the claims.

Example 1

Peach Germplasm and Crosses

The dw trait used in this study originated from the dwarf cultivar 'Valley Red' and was obtained from the University of California, Davis. 'Valley Red' trees were hybridized to produce peach populations segregating for the dwarf phenotype. An individual F2 tree, previously shown to be heterozygous, was selfed to produce a single segregating population of approximately 140 individuals which were used in the current study.

Example 2

DNA Extraction and Pnome Mapping

To map the peach dw trait from peach tree populations, a strategy for simultaneous genetic mapping and candidate gene identification using next-generation sequencing of pooled genomes, dubbed "pnomes" was utilized (Dardick et al. 2013. *Plant J.* 75:618-630). The pnomes strategy is based on sequencing a population(s) of segregating individuals pooled by a specific trait(s). In theory, the linkage of individual polymorphisms to a trait of interest should be measurable by calculating the abundance of each polymorphism within a given pnome assembled against a reference genome. Tightly linked polymorphisms should occur at high frequency in the pnome containing the trait while those same polymorphisms should be rare or absent in the pnome lacking the trait, and vice versa. Consequently, when graphed by nucleotide position, the data should produce a bell-shaped curve delineating the location of the trait. To test the efficacy of the pnomes strategy, DNA was extracted from 62 brachytic dwarf (BD) trees and 49 standard trees from a 2 year old field grown population derived from a selfed dw/+peach tree (KV040127). Extractions were done using the Omega bio-tek EZNA SQ Plant DNA extraction kit (Cat # D3095-01) which included an RNAse step. DNA concentrations were calculated using the Molecular Probes Quant-iT™ PicoGreen® dsDNA Assay (Life Technologies Cat # P11496). DNA from BD and Tall trees were pooled separately, with equal amounts of DNA from each tree in a pool. A total of 4 µg of pooled DNA was sent to Weill Cornell Medical College, Ithaca N.Y. for sequencing.

Genomics sequencing data was generated by the genomics resources core facility at Weill Cornell Medical College using an Illumina HiSeq 2000. Libraries for the Tall and the BD gDNA pools were sequenced in separate lanes. The gDNA library for the standard tree generated 286,020,940 raw reads. The BD library generated 261,319,154. These reads were imported into CLC Genomics Workbench version 6.5.2 (CLC BIO, Boston, Mass.) where they were trimmed based on quality (ambiguity limit of 2 nucleotides; quality limit of 0.05 Phred score) and length (reads less than 75 nucleotides were discarded) prior to analysis. After trimming, 272,365,448 remaining Tall pool reads, and 249,689,984 remaining BD pool reads were mapped to the *Prunus persica* v1.0 genome (Verde et al. 2013. *Nature Genetics* 45:487-494) using the following parameters: a mismatch cost of 2, an insertion cost of 3, a deletion cost of 3, length fraction 0.6, similarity cost of 0.96, no global alignment, auto-detect paired distance was selected, and non-specific matches were mapped randomly. 249,702,013 Tall pool reads and 223,437,725 reads from the BD pool were separately mapped to the peach genome. Sequence variant analysis for both BD and Standard populations was done by entering the mapping data into the CLC probabilistic variant detection function with the following parameters: non-specific matches and broken pairs were ignored, minimum coverage was 25, variant probability was 90, both forward and reverse reads were required, and the maximum expected variants was set at 2. The Tall pool had 308,097 variants (compared to the published peach reference genome), and the BD pool had 353,891 variants. Variants from the BD pool that had a frequency of <80% were removed as were those with a forward/reverse balance <0.1, and those with coverage >500. The remaining variants were further manually filtered by removing variants with frequencies in the Tall pool that were >50%. Variants on each chromosome were graphed separately by frequency over chromosome position.

Figure 1A:
FIGS. 1A-1D depict standard and brachytic dwarf peach trees.
Figure 1B:
Figure 1C:
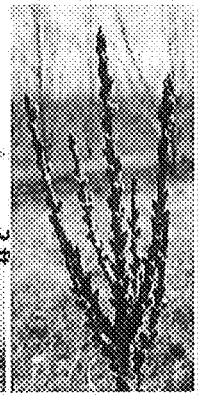
Figure 1D:
Figure 2A:
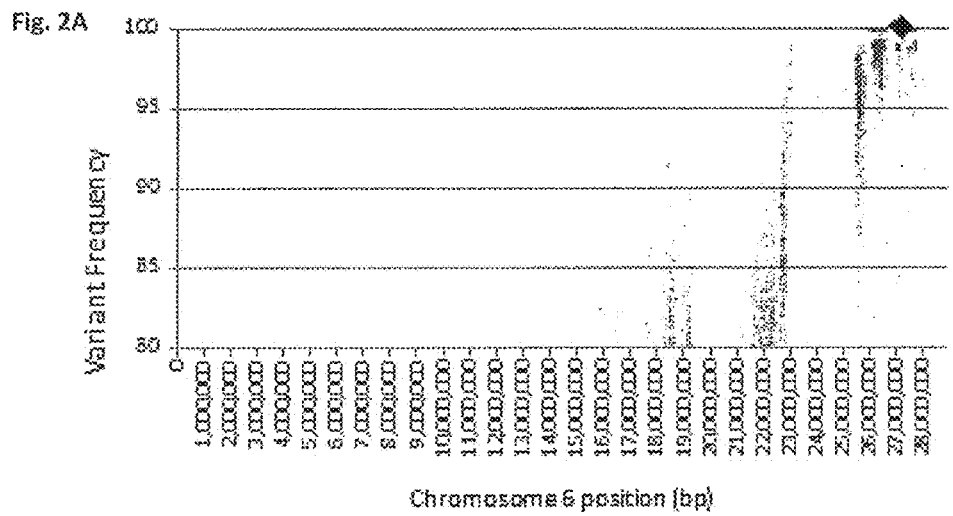
FIGS. 2A-2B depict the identification of the brachytic dwarf gene (dw) as an allele of Ppa018174, a GID1c homolog.

The variants from the dwarf pool were filtered using those present in the Tall pool (as described above) and those that remained were graphed by frequency over their chromosome position. Of the 3,434 variants that remained, 2,927 were located on chromosome 6, 7 were on chromosome 1, 29 were on chromosome 2, 27 on chromosome 3, 17 on chromosome 4, 4 on chromosome 5, 414 on chromosome 7, 4 on chromosome 8, and 2 on chromosome 9. Variants on chromosome 6 (which comprised 85% of the total number) produced a bell curve distribution associated with gene linkage, where the chromosome region under the peak is the anticipated location of the gene being mapped. The pnome map showed that the dw locus is located on the distal end of peach chromosome 6 (FIG. 2A).

Upon examination of the gene sequences in the dwarf pool across the mapped location, a point mutation leading to a premature stop codon (nonsense mutation) was found within gene Ppa018174, a putative orthologue of the *Arabidopsis* Gibberellic Acid receptor genes GA INSENSITIVE DWARF 1a (AtGID1a) and AtGID1c. *Arabidopsis* also contains a $3^{rd}$ GA receptor called GID1b. Ppa018174 showed 70% homology to AtGID1a and 80% homology to GID1b at the protein level. AtGID1A and AtGID1b have 94.8% similarity (using LALIGN; Huang and Miller. 1991. *Adv. Appl. Math.* 12:337-357) and have redundant functions (Griffiths et al., supra). A recent paper by El-Sharkaway et al. (2014. *Plant Mol. Biol.* 84:399-413) named this orthologous gene in japanese plum (*Prunus salicina*) PsIGID1c. Since PsGID1c shares 99.4% protein identity with the peach dw allele, for consistency, we named the peach brachytic dwarf gene PpeGID1c.

Figure 2B:
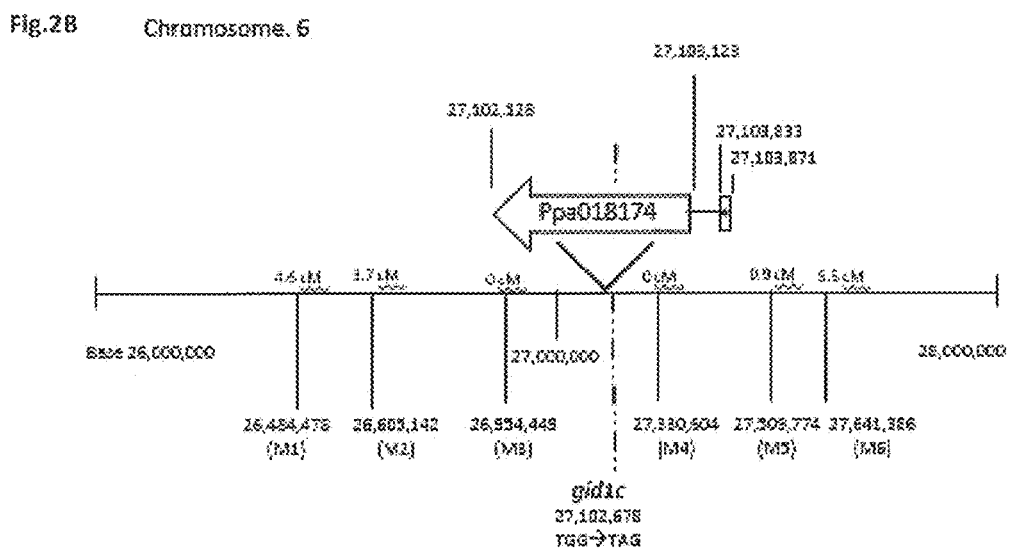

Following the pnome mapping, High Resolution Melt (HRM) marker analysis was performed on 109 individual dwarf and tall trees from the mapping population using primers that detected the presence of the gid1c mutation as well as identified SNPS at 200,000 base pair intervals flanking the nonsense SNP mutations (FIG. 2B, Table 1). Three pairs of primers were produced for SNPS that were located at ~200 kb distances from each other upstream and downstream of the GID1c homologue. An additional pair of primers was designed for a SNP within GID1c (Table 1). HRM assays were performed using MeltDoctor™ HRM Master Mix (Applied Biosystems, USA) according to the manufacturer's protocol and were run using a ViiA™ Real-Time PCR System instrument (Applied Biosystems, USA). Thermocycling parameters for amplification stage were 95° C. for 10 min, followed by 40 cycles of 95° C. for 15 s and 60° C. for 40 s. For the HRM stage, fluorescence recordings were made over the range of 60-95° C. by increments of 0.025° C./s. DNA controls consisting of dominant homozygous, heterozygous and recessive homozygous plant DNA were included in triplet to confirm marker scoring.

TABLE 1

SNP position and base change for HRM markers.

| Marker | SNP Position | SNP | Primer | Sequence (5'→3') | SEQ ID NO: |
|---|---|---|---|---|---|
| M1 | 26,484,478 | G/A | F | CCGTTTGCATAGATCCGTT | 6 |
|    |            |     | R | TGGGGATTCGAGATCCC | 7 |
| M2 | 26,605,142 | A/C | F | TCAAGTATTGGAAGCAGTTGTT | 8 |
|    |            |     | R | TTGCAACCATAGGTTGGGACT | 9 |
| M3 | 26,954,449 | A/G | F | CAGAATGAGAAGGCAAGGC | 10 |
|    |            |     | R | ATCTCCAATGCAATTCGCC | 11 |
| gid1c | 27,102,678 | C/T | F | TAAGCCACGATCTAGAGTTGACC | 12 |
|    |            |     | R | GTAAATTACCGCCGGGCA | 13 |
| M4 | 27,330,604 | G/A | F | GCCCGAGGCAGAGTTATT | 14 |
|    |            |     | R | GGTCCGTTTCCTATGCG | 15 |
| M5 | 27,509,774 | G/A | F | CGCCATGGTTGGTTTTG | 16 |
|    |            |     | R | CCCTCACCTTCTCTGCCTC | 17 |
| M6 | 27,641,386 | A/G | F | GCTGCTTCAAGGCCTTCAT | 18 |
|    |            |     | R | GGACCCCACTTGAATGAAATT | 19 |

HRM analysis found all dwarf trees to be homozygous for gid1c while the tall trees were either heterozygous or homozygous for the wild type gene (Table 2). Recombination events detected by markers narrowed the locus to an approximately 400 kb region and supported GID1c as the primary candidate DW gene (Table 2). A score of 1 indicates that a plant is homozygous for the HRM marker SNP associated with the Tall phenotype. A score of 2 indicates that a plant is heterozygous for the marker SNP (there is one Tall-associated SNP and one dwarf-associated SNP). A score of D indicates that a plant is homozygous for the dwarf-associated SNP. A transition of a score of 1 to a score of 2 or a 2 to a D between consecutive markers indicates a single recombination event. A transition from a 1 to a D or vice versa indicates a double recombination event.

TABLE 2

HRM scores of the seven markers used to screen 109 F2 plants from a dwarf-segregating population.

| Phenotype | plant # | M1 | M2 | M3 | gid1c | M4 | M5 | M6 |
|---|---|---|---|---|---|---|---|---|
| Brachytic Dwarf | 1 | D | D | D | D | D | D | D |
|  | 2 | D | D | D | D | D | D | D |
|  | 3 | F | D | D | D | D | D | D |
|  | 4 | D | D | D | D | D | D | D |
|  | 5 | D | D | D | D | D | D | D |
|  | 6 | D | D | D | D | D | D | D |
|  | 8 | D | D | D | D | D | D | D |
|  | 9 | D | D | D | D | D | D | D |
|  | 10 | 2 | 2 | D | D | D | D | D |
|  | 11 | D | D | D | D | D | D | D |
|  | 12 | D | D | D | D | D | D | D |
|  | 13 | 2 | 2 | D | D | D | D | D |
|  | 14 | D | D | D | D | D | D | D |
|  | 15 | D | D | D | D | D | D | D |
|  | 16 | 2 | 2 | D | D | D | D | D |
|  | 17 | D | D | D | D | D | D | D |
|  | 18 | D | D | D | D | D | D | D |
|  | 19 | D | D | D | D | D | D | D |
|  | 20 | D | D | D | D | D | D | D |
|  | 21 | D | D | D | D | D | D | D |
|  | 22 | D | D | D | D | D | D | D |
|  | 23 | D | D | D | D | D | D | D |
|  | 24 | D | D | D | D | D | D | D |
|  | 25 | D | D | D | D | D | D | D |
|  | 26 | D | D | D | D | D | D | D |

TABLE 2-continued

HRM scores of the seven markers used to screen 109 F2 plants from a dwarf-segregating population.

| Phenotype | plant # | M1 | M2 | M3 | gid1c | M4 | M5 | M6 |
|---|---|---|---|---|---|---|---|---|
| | 27 | D | D | D | D | D | D | D |
| | 28 | D | D | D | D | D | D | D |
| | 29 | D | D | D | D | D | D | D |
| | 30 | D | D | D | D | D | D | D |
| | 31 | D | D | D | D | D | D | D |
| | 32 | D | D | D | D | D | D | D |
| | 33 | D | D | D | D | D | D | D |
| | 35 | D | D | D | D | D | D | D |
| | 37 | D | D | D | D | D | D | D |
| | 38 | D | D | D | D | D | D | D |
| | 39 | D | D | D | D | D | D | D |
| | 40 | D | D | D | D | D | D | D |
| | 41 | D | D | D | D | D | D | D |
| | 42 | D | D | D | D | D | D | D |
| | 43 | D | D | D | D | D | D | D |
| | 44 | D | 2 | D | D | D | D | D |
| | 45 | D | D | D | D | D | D | D |
| | 46 | D | D | D | D | D | D | D |
| | 47 | D | D | D | D | D | D | D |
| | 48 | D | D | D | D | D | D | D |
| | 49 | D | D | D | D | D | D | D |
| | 50 | D | D | D | D | D | D | D |
| | 51 | D | D | D | D | D | D | D |
| | 52 | D | D | D | D | D | D | D |
| | 53 | D | D | D | D | D | D | D |
| | 54 | D | D | D | D | D | D | D |
| | 55 | D | D | D | D | D | D | D |
| | 56 | D | D | D | D | D | D | D |
| | 58 | D | D | D | D | D | D | D |
| | 59 | D | D | D | D | D | D | D |
| | 60 | D | D | D | D | D | D | F |
| | 61 | D | D | D | D | D | D | D |
| | 62 | D | D | D | D | D | D | D |
| | 63 | D | D | D | D | D | D | D |
| Tall Control | 1 | 2 | 2 | 2 | 2 | 2 | 2 | 2 |
| | 2 | 2 | 2 | 2 | 2 | 2 | 2 | 2 |
| | 3 | 1 | 1 | 1 | 1 | 1 | 1 | 1 |
| | 4 | 2 | 2 | 2 | 2 | 2 | 2 | 2 |
| | 5 | 1 | 1 | 1 | 1 | 1 | 1 | 2 |
| | 6 | 2 | 2 | 2 | 2 | 2 | 2 | 2 |
| | 7 | 2 | 2 | 2 | 2 | 2 | 2 | 2 |
| | 8 | 2 | 2 | 2 | 2 | 2 | 2 | 2 |
| | 9 | 1 | 1 | 1 | 1 | 1 | 1 | 1 |
| | 10 | 2 | 2 | 2 | 2 | 2 | 2 | 2 |
| | 11 | 2 | 2 | 2 | 2 | 2 | 2 | 2 |
| | 12 | 2 | 2 | 2 | 2 | 2 | 2 | 2 |
| | 13 | 2 | 2 | 2 | 2 | 2 | 2 | 2 |
| | 14 | 1 | 1 | 1 | 1 | 1 | 1 | 1 |
| | 15 | 2 | 2 | 2 | 2 | 2 | 2 | 2 |
| | 16 | 2 | 2 | 2 | 2 | 2 | 2 | 2 |
| | 17 | 2 | 2 | 2 | 2 | 2 | 2 | 2 |
| | 18 | 2 | 2 | 2 | 2 | 2 | 2 | D |
| | 19 | 2 | 2 | 2 | 2 | 2 | 2 | 2 |
| | 20 | 2 | 2 | 2 | 2 | 2 | 2 | 2 |
| | 21 | 1 | 1 | 1 | 1 | 1 | 1 | 1 |
| | 22 | 1 | 1 | 1 | 1 | 1 | 1 | 1 |
| | 23 | 2 | 2 | 2 | 2 | 2 | 2 | 2 |
| | 24 | 1 | 1 | 1 | 1 | 1 | 1 | 1 |
| | 25 | 2 | 2 | 2 | 2 | 2 | 2 | 2 |
| | 26 | 1 | 1 | 1 | 1 | 1 | 1 | 1 |
| | 27 | 1 | 1 | 1 | 1 | 1 | 1 | 1 |
| | 28 | 2 | 2 | 2 | 2 | 2 | 2 | 2 |
| | 29 | 1 | 1 | 1 | 1 | 1 | 1 | 1 |
| | 30 | 1 | 1 | 1 | 1 | 1 | 1 | 1 |
| | 31 | 1 | 1 | 1 | 1 | 1 | 1 | 1 |
| | 32 | 2 | 2 | 2 | 2 | 2 | 2 | 2 |
| | 33 | 2 | 2 | 2 | 2 | 2 | 2 | 2 |
| | 34 | 1 | 1 | 1 | 1 | 1 | 1 | 1 |
| | 35 | 1 | 1 | 1 | 1 | 1 | 1 | 1 |
| | 36 | 2 | 2 | 2 | 2 | 2 | 2 | 2 |
| | 37 | 2 | 2 | 2 | 2 | 2 | 2 | 1 |
| | 38 | 2 | 2 | 2 | 2 | 2 | 2 | 2 |
| | 39 | 1 | 1 | 1 | 1 | 1 | 1 | 1 |
| | 40 | 2 | 2 | 2 | 2 | 2 | 2 | 2 |
| | 41 | 1 | 1 | 1 | 1 | 1 | 1 | 1 |
| | 42 | 2 | 2 | 2 | 2 | 2 | 2 | 2 |
| | 43 | 2 | 2 | 2 | 2 | 2 | 2 | 1 |
| | 44 | 1 | 1 | 1 | 1 | 1 | 1 | 1 |
| | 45 | 2 | 2 | 2 | 2 | 2 | 2 | 2 |
| | 46 | 1 | 1 | 1 | 1 | 1 | 1 | 1 |
| | 47 | 2 | 2 | 2 | 2 | 2 | 2 | 2 |
| | 48 | 1 | 1 | 1 | 1 | 1 | 1 | 1 |
| | 49 | 1 | 1 | 1 | 1 | 1 | 1 | 1 |
| | 50 | 2 | 2 | ? | 2 | 2 | D | 2 |
| Recombination event # | | 5 | 4 | 0 | 0 | 0 | 1 | 6 |
| Total plants screened | | 108 | 109 | 108 | 109 | 109 | 109 | 109 |
| Percent recombination | | 4.6 | 3.7 | 0.0 | 0.0 | 0.0 | 0.9 | 5.5 |

Example 3

Plum Transformation

A 249 bp fragment (SEQ ID NO:4) of the peach GID1c gene (Ppa018174) (SEQ ID NO:1) was amplified from DNA derived from the standard size peach variety 'True Gold' using the following primers: GID1a-silence-F1 (5'ATG-GATGGACAGCCCTGC; SEQ ID NO:20) and GID1a-silence-R1 (5'GGTCTTGGATGGTGACAAAGTATTT; SEQ ID NO:21). The resulting fragment was cloned into the Invitrogen pCR™8/GW/TOPO® TA vector, and then transferred to into the pHELLSGATE 8.0 vector in a hairpin arrangement via Gateway cloning technology (Life Technologies, Frederick, Md.). This fragment (SEQ ID NO:4) was chosen due to a lack of similarity to GID1b (FIG. 6) in order to avoid silencing both genes.

The pHELLSGATE 8.0 plasmid containing peach GID1a gene were transformed into Agrobacterium tumefaciens strain GV3101. The gene construct was engineered into European plum (Prunus domestica L) following the protocol of Petri et al. (2012. Methods Mol. Biol. 847:191-199). Cold (4° C.)—stored seeds of 'Bluebyrd' plum were used for transformation. Briefly, the seeds were first cracked to remove stony seed coat, surface sterilized with 15% commercial bleach for 15 minutes, washed three times with sterile water, and the hypocotyl slices were excised from the zygotic embryos under a laminar flow hood using a stereomicroscope. After incubating for 20 minutes in an Agrobacterium suspension, the transformed hypocotyl sections were cultured for 3 days in co-cultivation medium. Finally the hypocotyl sections were plated in antibiotic (80 mg/l kanamycin) selection medium to produce transgenic shoots. The kanamycin resistant transgenic shoots were multiplied in plum shoot multiplication medium, rooted, acclimatized in the growth chamber and planted in 6-9" pots in a temperature controlled greenhouse to evaluate growth and development.

To further test if GID1c is responsible for the brachytic dwarf phenotype, a GID1c RNAi-silencing vector comprising SEQ ID NO:4 was transformed into European plum (Prunus domestica), a transformable species that is closely related to peach. The resulting trees exhibited various degrees of dwarfism and significantly shorter internodes when compared to control plants containing an empty vector (FIG. 3A-C). The expression level of GID1c in select plums lines was examined. A correlation between plant height and gene expression was observed (FIG. 3C, D). Trees with high levels of GID1c expression (such as those in line 1) were significantly taller than those with lower levels of GID1c expression (such as the trees in lines 2 and 3), while those with intermediate expression had intermediate heights (FIG. 3C, D).

Example 4

GID1c Gene Expression

Expression profiles of GID1c and the other peach GID1 GA receptor gene GID1b (Ppe008128), were assessed via qPCR analysis on an existing tissue-specific RNA collection (described in Dardick et al. 2013, supra). Total RNA was extracted from frozen samples using E.Z.N.A SQ Total RNA Kit (Omega Bio-tek, Inc., USA), according to the manufacturer's instructions. Leaf tissue was used for extraction and for expression analysis in transgenic plums. Resulting RNA samples were then treated with DNase I. qPCR reactions were carried out using SuperScript III Platinum SYBR Green One-Step qRT-PCR Kit with ROX (Invitrogen Corp., USA) and the reaction mix was produced according to the manufacturer's protocol. Gene-specific primers were synthesized for the GID1c and GID1b genes. For the GID1c gene, the forward primer was 5'-GCTCTATACAGACGGTGGTTCCAT-3' (SEQ ID NO:22) and the reverse primer was 5'-CCCATCAACTGGTTTTGCATTGGC-3' (SEQ ID NO:23). For the GID1b gene, the forward primer was 5'-GCTGGCAGTAATGAAGTCAACGTC-3' (SEQ ID NO:24) and the reverse primer was 5'-CTCTGCCAACTCACGGTTGAATGT-3' (SEQ ID NO:25). The qPCR was run according to the following parameters: cDNA synthesis step at 50° C. for 5 min, followed by PCR reactions at 95° C. for 5 min and 40 cycles of 95° C. for 15 s, 60° C. for 30 s, and final 40° C. for 1 min. Standard errors of the means from three independent biological replicates were calculated.

GID1c expression correlates with a role in vegetative shoot growth. Both genes were expressed in the flower, fruit, leaf, root, and shoot apical meristem tissues (FIG. 4). However, PpeGID1c was more highly expressed in apical and root tissues while PpeGID1b was more highly expressed in the flower and fruit tissues. Expression of both GA receptors could not be detected in dormant tissues.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A RNAi construct comprising a GA Insensitive Dwarf 1c (GID1c) sense polynucleotide fragment comprising SEQ ID NO:4 and a GID1c antisense polynucleotide fragment complementary to SEQ ID NO:4.

2. A vector comprising a promoter operably linked to the RNAi construct of claim 1.

3. An isolated host cell comprising the vector of claim 2.

4. The isolated host cell of claim 3, wherein said isolated host cell is a *Prunus* cell.

5. The host cell of claim 4, wherein said host cell is a cell from any one of *Prunus persica, Prunus domestica, Prunus avium, Prunus salicina* and *Prunus armeniaca*.

6. A method of producing a transformed *Prunus* plant having shorter internodes than a wild-type *Prunus* plant's internodes length, said method comprising: (i) transforming wild-type *Prunus* plant cells with the recombinant vector comprising a polynucleotide encoding a sense fragment and antisense fragment of GID1c gene, wherein said sense fragment comprises SEQ ID NO:4 and said antisense fragment is complementary to said sense fragment to form transgenic *Prunus* plant cells; (ii) selecting at least one transgenic *Prunus* plant cell that expresses said recombinant vector, wherein said recombinant vector produces said sense fragment and antisense fragment which form a double stranded RNA to produce at least one selected transgenic *Prunus* plant cell; and (iii) growing said at least one selected transgenic *Prunus* plant cell that expresses said recombinant vector into a transgenic *Prunus* plant, wherein said double stranded RNA produced by said recombinant vector reduces said GID1c's expression level in said selected transgenic *Prunus* plant cell compared to said GID1c's expression level in said wild-type *Prunus* plant cell, and said transgenic *Prunus* plant has shorter internodes compared to said wild-type *Prunus* plant's internode length.

7. A transgenic *Prunus* plant produced by the method of claim 6 or the progeny thereof, wherein said transgenic *Prunus* plant and progeny thereof have shorter internodes compared to a wild-type non-transformed *Prunus* plant's internodes length; wherein said transgenic *Prunus* plant and said progeny thereof produce a double stranded RNA comprising a sense fragment and antisense fragment of GID1c gene, wherein said sense fragment comprises SEQ ID NO:4 and said antisense fragment is complementary to said sense fragment.

8. A transgenic *Prunus* cell comprising a vector comprising a promoter operably linked to the RNAi construct of claim 1, wherein a transgenic *Prunus* plant regenerated from said transgenic *Prunus* cell produces said RNAi construct, and said RNAi construct reduces expression of GID1c gene, resulting in said transgenic *Prunus* plant have shorter internodes relative to internode length in a wild-type *Prunus* plant.

9. A transgenic seed of the transgenic *Prunus* plant of claim 7, wherein said transgenic seed produce a double stranded RNA comprising a GID1c sense polynucleotide fragment comprising the sequence of SEQ ID NO:4 and a GID1c antisense polynucleotide fragment comprising a sequence complementary to SEQ ID NO:4.

10. Transgenic plants, transgenic plant cells, transgenic plant parts, and transgenic plant seeds from any one of *Prunus persica, P. domestica, P. avium, P. salicina* and *P. armeniaca* which have been transformed with the vector of claim 2, wherein said transgenic plants, transgenic plant cells, transgenic plant parts, and transgenic plant seeds produce a double stranded RNA comprising a sense fragment and antisense fragment of GID1c gene, wherein said sense fragment comprises SEQ ID NO:4 and said antisense fragment is complementary to said sense fragment; and wherein said double stranded RNA causes said transgenic plants and a transgenic plant obtained from said transgenic plant cells, said transgenic plant parts, and said transgenic plant seeds to produce less GID1c compared to GID1c levels in a wild-type plant which causes said transgenic plants to have shorter internodes than said wild-type plant's internode length.

* * * * *